US012151052B2

(12) United States Patent
Joshi

(10) Patent No.: US 12,151,052 B2
(45) Date of Patent: Nov. 26, 2024

(54) FLAMELESS ENERGIZED EMANATOR

(71) Applicant: Microlin, LLC

(72) Inventor: Ashok V. Joshi, Salt Lake City, UT (US)

(73) Assignee: Microlin, LLC, Salt Lake City, UT (US)

( * ) Notice: Subject to any disclaimer, the term of this patent is extended or adjusted under 35 U.S.C. 154(b) by 822 days.

(21) Appl. No.: 17/322,849

(22) Filed: May 17, 2021

(65) Prior Publication Data

US 2022/0168457 A1 Jun. 2, 2022

Related U.S. Application Data

(60) Provisional application No. 63/133,686, filed on Jan. 4, 2021, provisional application No. 63/120,664, filed on Dec. 2, 2020.

(51) Int. Cl.
*A61L 9/03* (2006.01)
*A01M 1/20* (2006.01)

(52) U.S. Cl.
CPC ........... *A61L 9/037* (2013.01); *A01M 1/2061* (2013.01); *A61L 2209/21* (2013.01)

(58) Field of Classification Search
CPC ........ A61L 9/037; A61L 9/03; A61L 2209/21; A01M 1/2061
See application file for complete search history.

(56) References Cited

U.S. PATENT DOCUMENTS

2008/0050690 A1 2/2008 Madan et al.
2008/0208162 A1* 8/2008 Joshi ................. A61M 37/0015 604/291
2010/0308126 A1* 12/2010 Gruenbacher ............ A61L 9/04 239/6

FOREIGN PATENT DOCUMENTS

CN 1293705 A * 5/2001 .......... A01M 1/2061
CN 105769550 7/2016
GB 2275608 9/1994
GB 2275608 A * 9/1994 ............... A61L 9/03

OTHER PUBLICATIONS

PCT International Search Report and Written Opinion, mailed Feb. 22, 2022.

* cited by examiner

*Primary Examiner* — Shawntina T Fuqua
(74) *Attorney, Agent, or Firm* — Brian C. Trask

(57) ABSTRACT

An energized assembly to disseminate a treatment agent in vapor phase to a local environment. The assembly includes an emanator element to hold treatment agent, and a flameless energizing source to facilitate volatization of the treatment agent. Preferred embodiments operate for a period of time of between about 4 and 8 hours, and can then be discarded. Typically, a housing associates the treatment agent and the energizing source. Embodiments may sometimes include one or more of: a gas-tight boundary element, a thermal transfer element, a trigger mechanism, a safety mechanism, a termination mechanism, a time-delay mechanism, solidized treatment agent to avoid spills, and a sequestering arrangement.

20 Claims, 13 Drawing Sheets

266
100
190
180
145
135
288
292
274
372
200
130
110
120
140
210
230
225
150
160
220
256
334
170

FLAMELESS ENERGIZED EMANATOR

RELATED APPLICATIONS

This application claims the benefit under 35 U.S.C. 119(e) of the filing date of Provisional Application Ser. No. 63/120,664, filed Dec. 2, 2020, for "ENERGIZED EMANATOR"; and Ser. No. 63/133,686, filed Jan. 4, 2021, for "ENERGIZED EMANATOR", the entire disclosures of which are hereby incorporated herein by this reference.

BACKGROUND

Field of the Invention

This invention relates to devices configured to dispense a treatment agent in vapor phase into a local environment and at an enhanced rate compared to surface evaporation from a quantity of the treatment agent in liquid phase at room temperature in undisturbed air.

State of the Art

Several ways are known to treat a local environment with a dispersed treatment fluid. One way to treat a local environment is to simply spray aerosol scent or mosquito repellant into the air. Devices such as perfumed or scented candles are available to create a pleasing smell in a local environment. Citronella candles are commercially available for insect abatement, and may be burned when treatment of a local area is desired. For mosquito relief, various machines may be employed to burn propane and emit a fog of repellant or poison. Some machines attract mosquitos and employ suction to capture them in a bag. Other devices attract insects, and kill them with a spark of electricity. These currently available products either lack sufficient efficacy, are cumbersome to use, or are too costly to gain wide acceptance. It would be an improvement to provide an effective product that is simple to use and sufficiently low cost to permit its disposal after a single use.

BRIEF SUMMARY OF THE INVENTION

Embodiments include an emanator element, a treatment agent associate with the emanator, and an energizing source to enhance emanation of the treatment agent in vapor phase. An emanator element typically has a surface area disposed in operable association with a volume in which to hold a quantity of treatment agent. Treatment agent volatizes, sublimates, or evaporates from the surface area to form treatment agent in vapor phase. The flameless energizing heat source may be disposed in a variety of operable configurations with the volume to apply heat energy to the treatment agent therein. A workable emanator element includes a material selected from the group consisting of cotton, paper, cellulose, woven textile or random mat or 3-dimensional structure comprising natural or synthetic fibers, natural or synthetic open or closed cell sponge, high surface area (HSA) materials having a surface area greater than 10 $m^2$/gm, diffusion membrane, and the like.

A workable treatment agent may be selected from scented oil, medicament, and insect repellant. In some cases, treatment agent may be in fluid phase. Sometimes, the treatment agent may be provided in a solidified form to resist spills and mess. In one such case, treatment agent fluid may be uptaken by a high surface area material from which treatment agent vapor may be released. Sometimes, the treatment agent may be provided in solid phase at room temperature. Heat energy may be applied to a treatment agent that is in liquid phase, solid phase, or solidified form to enhance broadcast of treatment agent in vapor phase to a local environment.

Desirably, the assembly includes a housing configured to contain the emanator and the heat source. An exemplary housing includes a plurality of apertures to permit migration of treatment agent in vapor state from the surface area to a local environment. A housing can be configured to define a safety perimeter to resist contact of the emanator with a child's mouth. A preferred housing includes a base configured to support the energized assembly on top of a surface under the influence of gravity. Certain housings may include an upstanding wall to hold apertures through which vapor may pass to the local environment. One housing may also include a cap to cover a volume defined inside the housing. It is within contemplation that the housing and cap may be configured to cooperate upon assembly of the emanating assembly to resist nondestructive disassembly and unauthorized access to the emanator element. In some cases, the housing can include a hook configured to support the assembly from a cooperating perch.

A workable heat source may be selected from the group consisting of chemicals arranged to generate an on-demand exothermic reaction, and an electrical circuit comprising a dry or wet cell battery or capacitor disposed in a heat-generating configuration.

Certain embodiments may include a removable gas barrier arranged to resist initiation of an exothermic chemical reaction associated with the energizing heat source. Embodiments may include a time-delay mechanism to delay activation of the heat source until after a period of time subsequent to first deployment of the assembly to treat a local environment. An embodiment may include a heat conducting element disposed between the heat source and the volume to facilitate heat transfer from the energizing heat source toward the volume. One workable heat conducting element is metallic foil.

Embodiments may optionally include a termination mechanism configured to resist further emanation of treatment agent in vapor state from the assembly to permit reuse of the apparatus at a subsequent time. Sometimes, an embodiment may include a trigger mechanism configured to initiate an exothermic reaction associated with the heat source. Embodiments may include a safety mechanism to resist undesired operation of the trigger mechanism. Embodiments may include an alternative safety mechanism to resist user access to a harmful component of the assembly. An exemplary safety mechanism to resist unauthorized access includes closely spaced apart louvers disposed around a perimeter of a tamper-proof housing.

One preferred embodiment includes an emanator element configured as a shell of revolution about an open core, a volume of the shell to hold a treatment agent, the open core to hold a flameless heat source. A quantity of the treatment agent can conveniently be disposed in the volume. Treatment agent may sometimes be stored in the volume as a solid or solidified fluid. The currently preferred embodiment includes a heat source disposed in the open core, the heat source comprising an exothermic mixture of chemicals arranged for on-demand production of heat. A heat conducting element is disposed between the chemicals and the emanator element to facilitate an even temperature profile applied to the treatment agent. The preferred embodiment also includes a housing with a plurality of spaced apart rails to provide a plurality of discharge apertures for a vapor of the treatment agent, the housing being configured to resist disassembly and unauthorized access to the emanator element. Further, an air-tight packaging envelope is disposed to resist combination of oxygen from a local atmosphere with the exothermic chemicals.

An exemplary and substantially fully loaded embodiment includes an emanator element defining a volume in which to hold a treatment agent. Treatment agent can be a fluid. A quantity of the treatment agent is disposed in solidized form within the volume. A flameless heat source is disposed in operable association with the emanator, the heat source including an exothermic mixture of chemicals arranged for on-demand production of heat. A heat conducting element is disposed between the chemicals and the emanator element to promote application by the heat source of a uniform temperature profile onto the emanator. A housing is included to hold the emanator element in operable association with the heat source.

The housing of this fully loaded embodiment also includes a plurality of discharge pores or apertures for a vapor of the treatment agent, and can also be configured to resist disassembly and unauthorized access to the emanator element. A trigger mechanism may be provided to cause the heat source to generate heat on-demand. A safety mechanism can also be provided to resist undesired operation of the trigger mechanism. A gas generating element may be disposed to enhance flow of treatment agent in vapor phase from the apertures. A termination mechanism may be provided to interrupt generation of heat by the heat source to permit reuse of the apparatus at a subsequent time. Sometimes, a sequestering arrangement holds a first ingredient out of contact with a second ingredient prior to actuation of the trigger mechanism. The assembly is typically packaged inside an air-tight packaging envelope to resist combination of oxygen from a local atmosphere with the exothermic chemicals prior to placement in service to treat a local environment.

BRIEF DESCRIPTION OF THE DRAWINGS

In the drawings, which illustrate what are currently considered to be the best modes for carrying out the invention.

DETAILED DESCRIPTION OF THE ILLUSTRATED EMBODIMENTS

Reference will now be made to the drawings in which the various elements of the illustrated embodiments will be given numerical designations and in which the invention will be discussed so as to enable one skilled in the art to make and use the invention. It is to be understood that the following description is only exemplary of certain principles of the present invention, and should not be viewed as narrowing the claims which follow.

Figure 1:
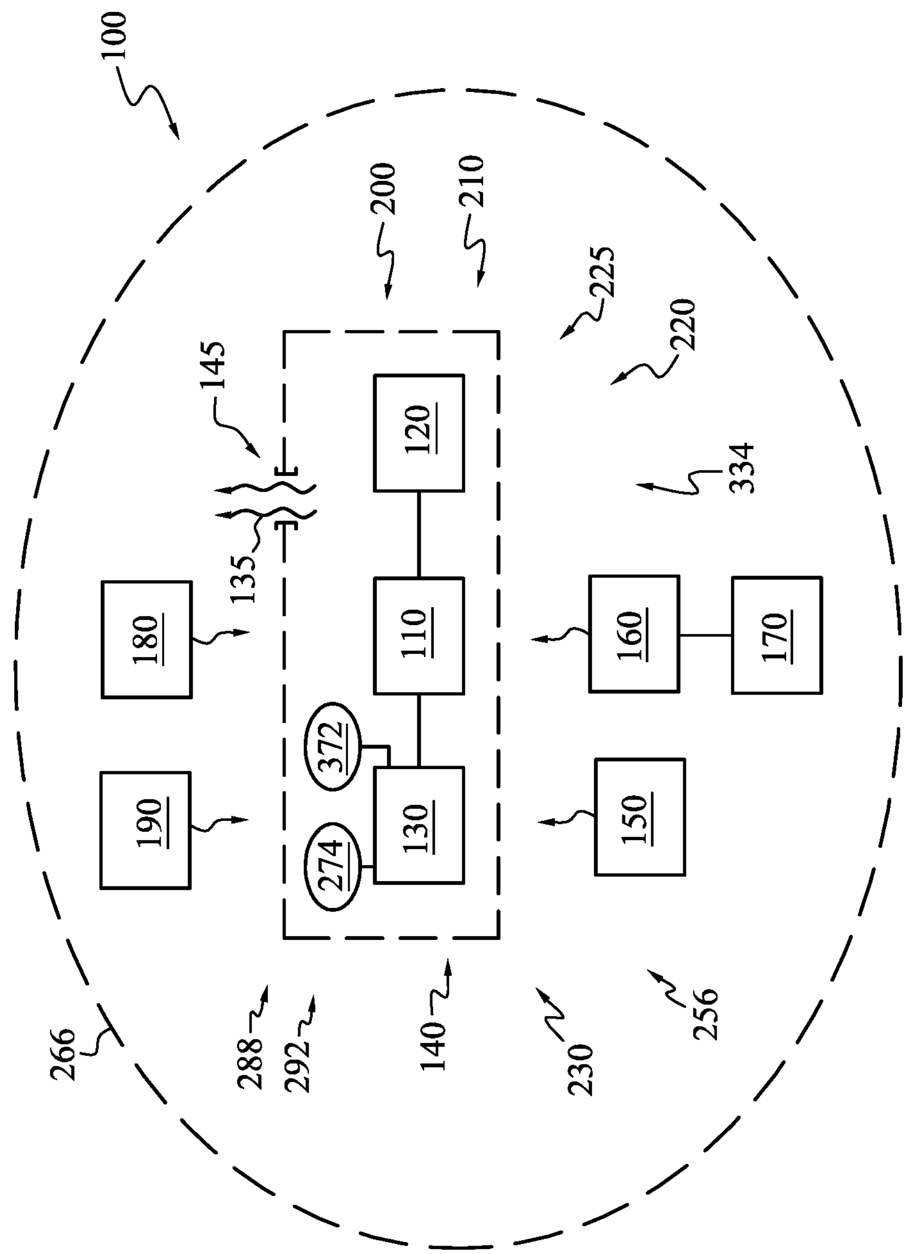
FIG. 1 is a schematic view of an exemplary device structured according to certain principles of the invention.

An energized emanator assembly according to certain principles of the invention is illustrated generally at 100 in FIG. 1. Embodiments 100 are typically self-contained, and desirably are portable to permit a person to easily move the assembly 100 to a desired location for operation to treat a local environment. Energized emanator assemblies 100 are conventionally used to apply a treatment fluid in vapor form to a local atmospheric environment. Treatment fluids may sometimes have relatively low volatility, and consequently, emanation of a vapor from those or other fluids may be enhanced to an efficacious degree by the energizing portion of an emanator assembly 100.

Embodiments 100 may be used, for nonexclusive examples, to treat a local atmosphere with a pleasing scent, beneficial treatment agent, or insect repellant. A local atmosphere may be stationary (e.g., due to an embodiment sitting on a table), or mobile (e.g., a user may wear an embodiment). Examples may be discussed below with reference to a particular fluid, such as insect repellant, but no limitation to any particular fluid is intended. Certain embodiments may be disposable after a single-use. Other embodiments may be recharged, or regenerated, to operate a plurality of times in succession. An emanator assembly 100 according to certain principles of the invention may operate for a period of several hours, one or more days, weeks, months, or even longer. One preferred emanator assembly 100 may be constructed to operate for a period of between about four and eight hours, and then be discarded. It is within contemplation that part or all of an emanator assembly 100 may be structured to facilitate its biodegradability.

An assembly 100 includes an emanator 110, a quantity of treatment fluid 120, and a flameless heat source 130 or other mechanism to energize the assembly and cause enhanced emanation of a treatment substance. An exemplary heat source 130 is configured and arranged to facilitate volatization of the treatment fluid. Consequently, treatment fluid 120 is dispensed in vapor form 135 to a local environment at an enhanced rate compared to evaporation from the surface of a quantity of that treatment fluid at room temperature in undisturbed air. In certain cases, a housing, generally indicated at 140, is provided to maintain the heat source 130 in operable association with the treatment fluid 120.

An exemplary emanator element 110 may be manufactured from, or include, material capable of uptaking treatment fluid for storage of treatment fluid inside a storage volume of, or associated with, the emanator element 110. In any case, a workable emanator material permits migration of treatment fluid from the storage volume to a surface area from which the treatment fluid may volatize (or evaporate), to dispense treatment fluid as a vapor into the local environment. By "uptaking" it is intended to mean a process including one of more of absorbing, adsorbing, diffusing, and chemically reacting. Workable emanator material nonexclusively includes cotton, paper, cellulose, woven textile or random mat or 3-dimensional structure comprising natural or synthetic fibers, natural or synthetic open or closed cell sponge, high surface area (HSA) materials having a surface area greater than 10 $m^2/gm$, diffusion membrane, and the like. An emanator 110 may be configured to resemble a paper cup, balloon, cylinder, cube, shapeless mass, or any other desired shape.

A workable treatment fluid 120 may encompass one or more of scented oil, medicament, and mosquito repellant. Volatile treatment fluid 120 within contemplation broadly include insect control chemicals, pest control chemicals, essential oils, and medicant chemicals. More specifically, operable insect control chemicals may include one or more of Deet, Picardine, Icaradin, IR3535, Metofluthrin, 1-methylpiperazine, or Permethrine, as well as Natural chemicals such as citriodiol and Oil of Lemon Eucalyptus. It is within contemplation that any volatizable fluid may be used in an assembly 100 as a treatment fluid 120 for application of the fluid's vapor 135 to a local environment.

A currently preferred fluid 120 is in a solidified form to reduce potential for spills and creation of a mess. By "solidified form" or "solidified fluid" it is intended to mean that the subject fluid is substantially confined in a medium to resist free-flowing fluid. Exemplary solidified fluid may be adsorbed or uptaken into a media such as a high surface area material. A workable fluid-holding media includes a material selected from the group including adsorbent high-surface area ceramic, Alumina, γ-form Alumina, Silica, activated carbon, carbon black, molecular sieves, and zeolite. A workable adsorbent material may also include a material selected from the group including bitumen, wood dust, paper mâchè, plastic clay, earth clay, cotton dust, ash, and cement powder. For purpose of this disclosure, a high-surface area material provides an available surface area that is greater than about 10 $m^2/g$ of material.

The resulting combination of fluid and media provides a fluid in usable form (e.g., for broadcast to a local environment, or to cause a chemical reaction), but does not present free flowing liquid. Consequently, solidified fluid will not cause a mess if the media providing the solidified fluid is spilled.

A flameless heat source 130 according to the instant invention is distinguished from a source of heat that is produced by conventionally burning a fuel in a flame (e.g., burning propane, butane, white gas, paraffin, oil, wood, paper, and the like). One currently preferred heat source 130 includes an arrangement of chemical ingredients that can react on-demand in a flameless exothermic chemical reaction. An exemplary such arrangement is found in commercially available hand or body warmers, such as hand warmers sold under the trade name "HOT and HOT". A workable flameless heat source 130 includes an electrical circuit configured to create heat. For example, a battery or capacitor may be placed in circuit to discharge through a resistor or heater element. A quickly-discharged battery itself may constitute a flameless heat source 130.

As is known, air-activated hand warmers can be made from Iron Fe, Cellulose C6H10O5, Activated carbon C, Water H2O, Polypropylene sack C3H6, Salt NaCl, and Vermiculite (MgFeAl)3(AlSi)4O10(OH)24H2O. Iron and Oxygen react producing heat. Water is the medium in which the Iron and the Oxygen react. Salt is a catalyst through the water speeding up the reaction. Activated carbon acts like charcoal in a BBQ grill and disperses the heat around the hand warmer. Vermiculite insulates the reaction in the hand warmer so it lasts longer. Cellulose takes up space/sometimes replaced with saw dust. Polypropylene sack keeps the moisture within the hand warmer.

In general, it is within contemplation to use some sort of self-heating chemical system using one or more primary components for exothermic reactions (such as calcium oxide), one or more porous components that can serve as a heat sink and conductor of heat as well as undergoing chemical transformations that release heat (zeolite), a weak acid (citric acid) for sustained modulation of temperature and pH. Exothermic reactions, mixing of some chemicals, sorption of certain chemicals, phase changes in chemicals, and dissolution of some chemicals in solvents release heat during these operations. The rate of heat generation coupled with mass and energy transfer rates to or from system(s) allows modulation of the temperature of systems. The modulation can be further enhanced by controlled release and availability of some of the components. This method provides with a class of self-heating product applications and focuses on the modulation of temperature through sequestering of reactions with different rates, heat release through dissolution, heat release through mixing, heat release through sorption, heat release through phase change as well as controlling mass and heat transfer rates.

Heat from the source 130 facilitates volatization of the treatment fluid 120. Consequently, a housing 140 may be provided to hold the heat source 130 in operable association with the treatment fluid 120. A workable housing 140 provides an avenue through which vaporized treatment fluid may be broadcast from stored or bulk treatment fluid to the local environment. For example, a housing 140 may include one or more aperture, generally 145, to permit passage of vapor from inside to outside of the housing. A workable aperture includes a pore in a diffusion membrane, space between fibers in a mat or cloth, window, door, gap, hole, louver, or other opening, and the like.

Sometimes, a housing 140 may also provide a protective or safety function. In one example, a housing 140 can be configured to resist access to stored treatment fluid 120 that is confined inside the housing. For example, a housing 140 may provide a protective physical barrier to resist placing a portion of an emanator 110 in a child's mouth, or to resist access of a child's tongue to a harmful chemical. One preferred housing 140 includes a closure element that resists nondestructive disassembly, and thereby, resists undesired access by a user to any potentially harmful contents inside the housing.

Assembly 100 may include a removable or openable gas barrier 150. A gas barrier 150 may operate to resist undesired initiation of an exothermic chemical reaction. An air barrier 150 may sometimes resist broadcast of vapors of treatment fluid prior to the time that a user places the assembly 100 into operation. An exemplary gas barrier 150 may be made from a sealed foil or plastic membrane. Location of a workable barrier 150 may be selected depending on its desired function. In one case, a barrier 150 may protectively envelop only a heat source 130 to restrict ingress of oxygen to an exothermic combination of ingredients. In another case, a barrier 150 may envelop the entire assembly 100, and can even function as packaging for sale. In certain cases, a volume inside barrier 150 may be evacuated, or filled with an inert gas during manufacture.

A trigger mechanism 160 may be included in certain embodiments of an assembly 100. When present, a trigger mechanism 160 may be operated to permit or cause flameless heat source 130 to generate heat. Many forms of an operable trigger mechanism 160 may be envisioned. A first exemplary trigger mechanism 160 can be constructed to pierce the wall of a container to combine ingredients for an exothermic reaction. A second exemplary trigger mechanism 160 may be constructed to release treatment fluid from confinement operably to place treatment fluid in contact with a heat source. Sometimes, a safety mechanism 170 may be included to resist undesired operation of a trigger mechanism 160.

Certain assemblies 100 may include a gas generating element 180. A workable gas generating element 180 can be disposed in association with treatment fluid 120 to facilitate evaporation of the treatment fluid by way of gas flow. Gas generators within contemplation nonexclusively include a fan and chemicals to cause effervescent chemical reactions.

One or more thermally conducting element 190 may be included in an assembly 100. Desirably, the thermally conductive element 190 is arranged to facilitate transmission of heat from the heat source 130 to the treatment fluid 120. A workable heat conducting element 190 includes a metallic element, such as Aluminum foil. A heat conducting element 190 may also function as a barrier to confine one or more element, fluid, or vapor. In certain embodiments, a thermally conductive element 190 may be perforated or provide access openings to facilitate transmission of treatment fluid in vapor form 135.

In certain cases, an energized emanator assembly 100 may be constructed to place treatment fluid 120 (and/or sometimes, a constituent material of a heat source), in a solidized form. By "solidized" it is intended to mean that the treatment fluid 120 is in condition to resist spilling or otherwise leaking from the assembly 100. Free-flowing fluid is distinguished over solidized fluid. Exemplary solidized treatment fluid may be formed by a process including adsorption or uptake of treatment fluid into one or more high surface area material, diffusion or adsorption of treatment fluid into a rubber or rubber-like material, or sufficiently complete absorption of treatment fluid into a substrate. A workable solidized water source includes water-jello or water beads.

Sometimes, an emanator assembly 100 may include a termination mechanism 210 to stop the enhanced rate of emanation. An exemplary termination mechanism 210 may nonexclusively include: structure configured to permit sealing or resealing part or all of an emanator inside an air-tight envelope; structure configured to permit removal of the volatile fluid from an energizing environment of the emanator; structure configured to stop an exothermic reaction in a heat source 130, and the like.

It is currently preferred to provide an air-tight barrier element 220 to resist undesired emanation of treatment fluid from an assembly 100. In certain cases, a barrier 220 may function to resist access of oxygen from the atmosphere to combine with one or more material of the assembly 100. In other cases, a barrier 220 may simply confine treatment vapors 135 inside a volume. A workable barrier 220 may also function as unit packaging, including display packaging for sale of an assembly 100.

Certain embodiments 100 may include a sequestering arrangement, generally 225, for initial isolation of the treatment fluid from operable association with an emanator or heat source. For example, treatment fluid 120 may be stored in assembly 100 separately from an emanator 110. A user may then take action to place the operable ingredients together or create a working combination.

Further, an embodiment 100 may include a time-delay mechanism, generally 230. It is within contemplation that a time-delay mechanism 230 may function in various useful ways. One way can be to delay peak energization of the assembly 100 for an extended period of time subsequent to placement of the assembly into service and compared to timed energy release rate from a device lacking the delay mechanism. A workable time-delay mechanism 230 can be based on fundamental effect of one or more material properties, or may employ an actual digital, electronic, or mechanical timer.

Figure 2:
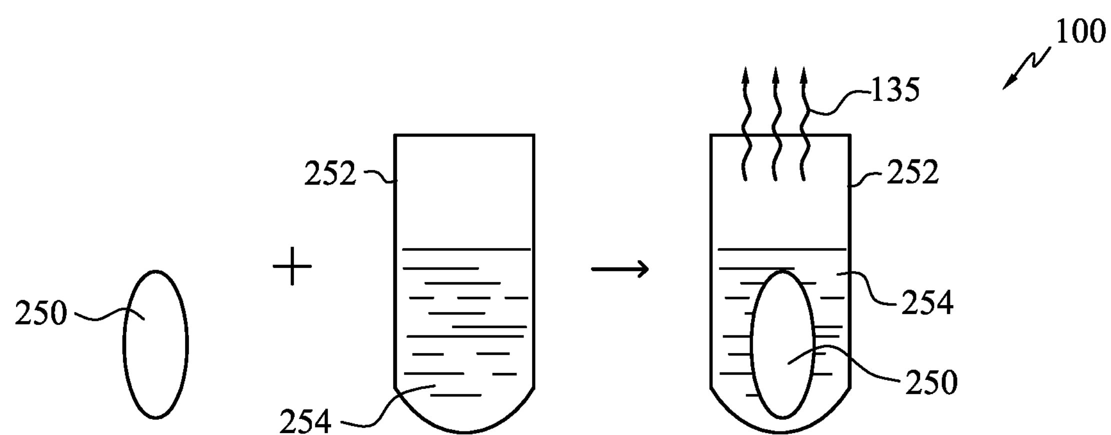
FIGS. 2 through 22 are schematic views in elevation of alternative embodiments within the ambit of FIG. 1.

The embodiment 100 illustrated in FIG. 2 illustrates principles of operation of certain energized emanator assemblies according to certain principles of the invention. Emanator assembly 100 in FIG. 2 includes a puck 250 that is introduced to a container 252 holding a fluid source 254. A currently preferred fluid (water) source 254 is in a solidified form, such as water-gelatin, to reduce potential for spills and creation of a mess. Workable solidified water 254 provides source of water that is sufficient to cause an exothermic reaction, and thereby, operate the emanator assembly 100. A puck 250 may be embodied as a tablet, or other convenient 3-dimensional object, or even in powder form. The composition of an exemplary puck 250 may include sodium bicarbonate, citric acid, and insect repellant. Calcium oxide or chloride chloride may be included in the puck 250 to generate on-demand heat during operation of emanator assembly 100.

Figure 3:
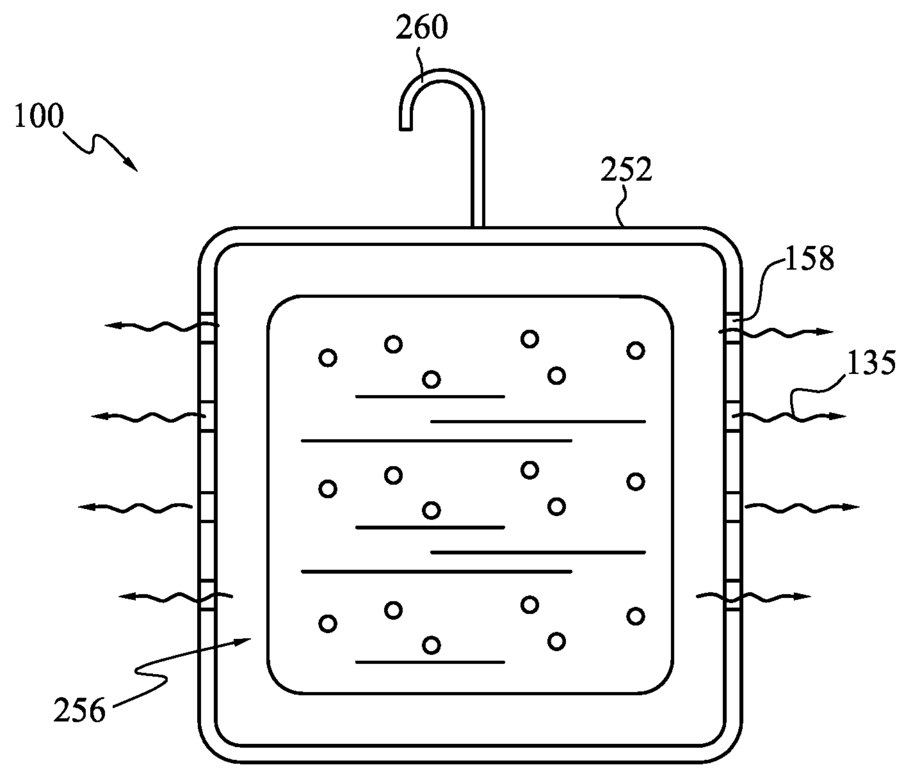

The embodiment 100 illustrated in FIG. 3 is exemplary of another energized emanator assembly according to certain principles of the invention. This emanator assembly 100 includes reactant materials, generally indicated at 256, confined inside a vented container 252. Exemplary reactant materials 256 may include heat-releasing material mixed with high surface area (HSA) material that is infiltrated with one or more treatment fluid. Reactant material 256 may be confined in any convenient manner, and may be embodied in a replaceable or rechargeable cartridge. An exothermic reaction within the reactant material 256 may be caused by exposure of the reactant material to a source of water, including humidity present in a local treatment atmosphere. Volatized treatment fluid in vapor phase 135 exits the container through one or more aperture 258.

A hook 260 exemplifies a structure to conveniently hold the emanator 100 for emanation of treatment fluid in vapor form 135 in a local environment. Illustrated hook 260 may be considered as generally representing an element configured to support the apparatus from a cooperating perch. As will be understood, a perch may be embodied as a stick, rod, upstanding plate edge, or other support structure arranged to cooperate with the hook 260. A cooperating hook and perch may function to associate an embodiment with a mobile or stationary local environment. For purpose of this disclosure, a hook specifically encompasses a spring loaded clip, and a perch specifically encompasses an article of clothing or a personal item such as a backpack or purse. Alternative holding or support structure within contemplation includes a simple base to support assembly 100 on a flat surface, such as a table top.

Figure 4:
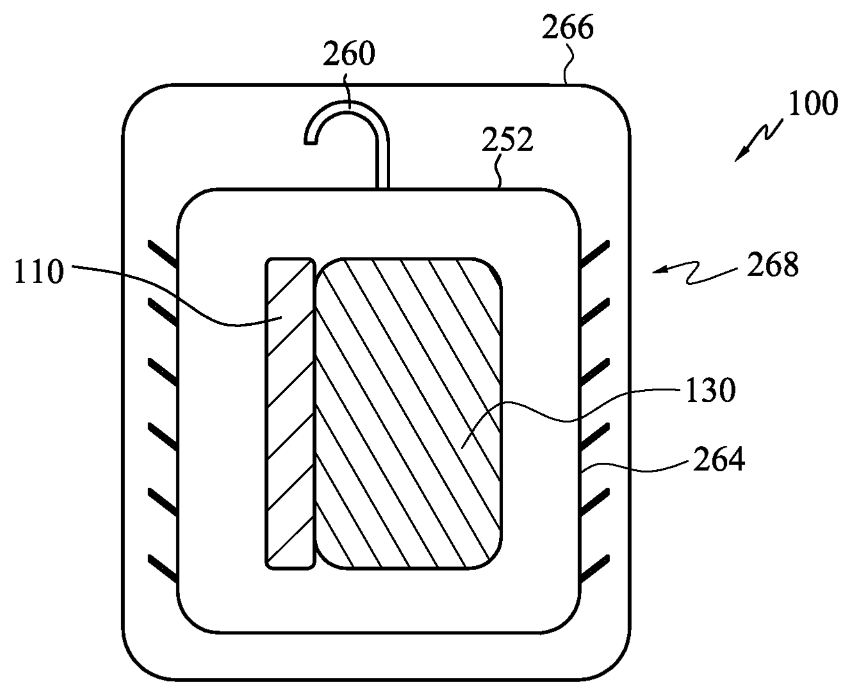

The embodiment 100 illustrated in FIG. 4 is exemplary of another energized emanator assembly according to certain principles of the invention. This emanator assembly 100 includes container 252 configured as a vented cage 264 to hold the constituent components, and an air-tight packaging envelope 266 to prevent premature exothermic reaction.

A workable cage 264 may include louvers, generally 268, or other aperture structure to permit emanation of vapor 135 from the emanator element 110 to a local environment. Humidity in ambient air may be used in combination with removal of the packaging envelope 266 as a triggering mechanism to start an exothermic reaction. The illustrated emanator element 110 is directly coupled in thermally operable registration with exothermic material confined inside the heat source 130. Activated thermal material energizes the treatment fluid 120 that is embedded or dispersed in the emanator 110, and a vapor 135 is emanated through a louver 268 to the local atmosphere.

Figure 5:
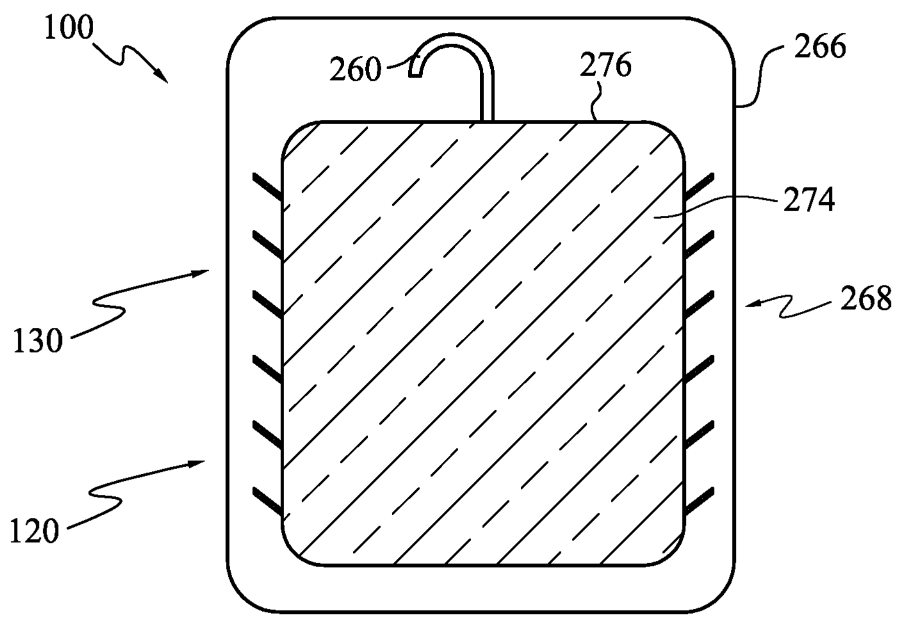

The embodiment 100 illustrated in FIG. 5 is exemplary of another energized emanator assembly according to certain principles of the invention. This emanator assembly 100 includes exothermic material 274 with treatment fluid dispersed within, loaded into, or uptaken by, the exothermic mixture 274 (or, sometimes the confining envelope 276), of an exothermic heat source 130. Operation of emanator assemblies 100 in FIGS. 4 and 5 are similar. Operation of the assemblies 100 may be started by simply opening the packaging envelope 266. These assemblies 100 will operate in an energized state until either the treatment fluid 120 is all evaporated, or the exothermic capability of the heat source 130 is exhausted.

Figure 6:
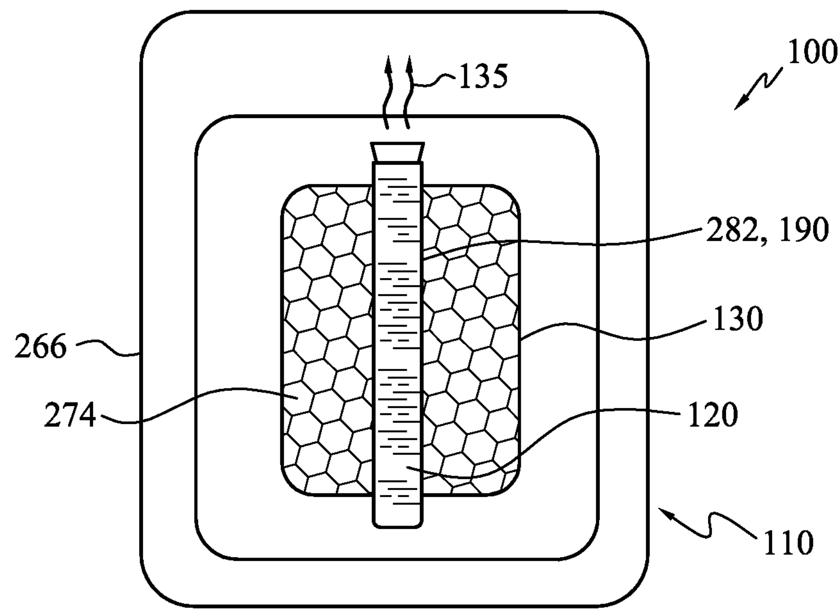

The embodiment 100 illustrated in FIG. 6 is exemplary of another energized emanator assembly according to certain principles of the invention. This emanator assembly 100 includes a thermally conductive housing 282 (e.g., a metal tube) to initially confine treatment fluid 120. Housing 282 is disposed in direct contact with a heat source 130 that is embodied as an exothermic patch. The thermally conductive housing 282 is exemplary of an optional heat conducting element 190 to transfer heat from the activated exothermal material 274 into the fluid 120, and thereby enhance emanation of a vapor 135 of the fluid 120 into the local environment.

Figure 7:
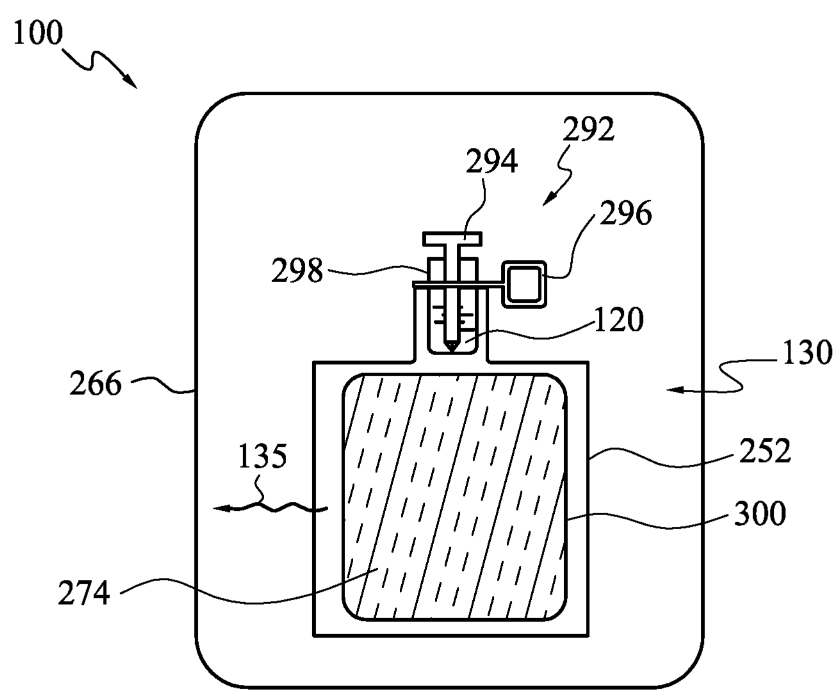

The embodiment 100 illustrated in FIG. 7 is exemplary of another energized emanator assembly according to certain principles of the invention. This emanator assembly 100 includes an initiating trigger mechanism, generally indicated at 292. The mechanism 292 includes a piercer 294, and a safety arrestor 296. Arrestor 296 resists undesired operation of the piercer 294. Treatment fluid 120 held in fluid container 298 is released by user operation of the piercer 294, and is allowed to contact a portion of the heat source 130. Fluid 120 may sometimes be dispersed into a porous bag 300, and/or may be uptaken in the exothermic material 274. The illustrated heat source 130 is structured similarly to a commercially available hand warmer. After the air-tight packaging 266 is removed, heat source 130 is activated by oxygen present in the air. Heat from the source 130 energizes the liquid 120, and vapor 135 is transmitted at an enhanced rate through porous container 252 into the local environment.

Figure 8:
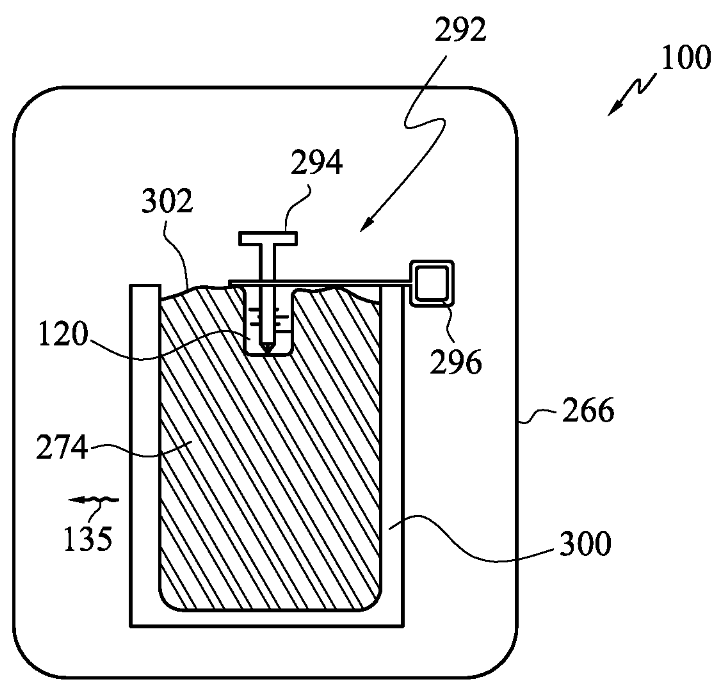

The emanator assembly 100 illustrated in FIG. 8 is substantially similar to that illustrated in FIG. 7. A difference is the arrangement of a membrane 302 that initially confines treatment fluid 120. Operation of the trigger mechanism 292 places released fluid 120 into direct contact with exothermic material 274.

Figure 9:
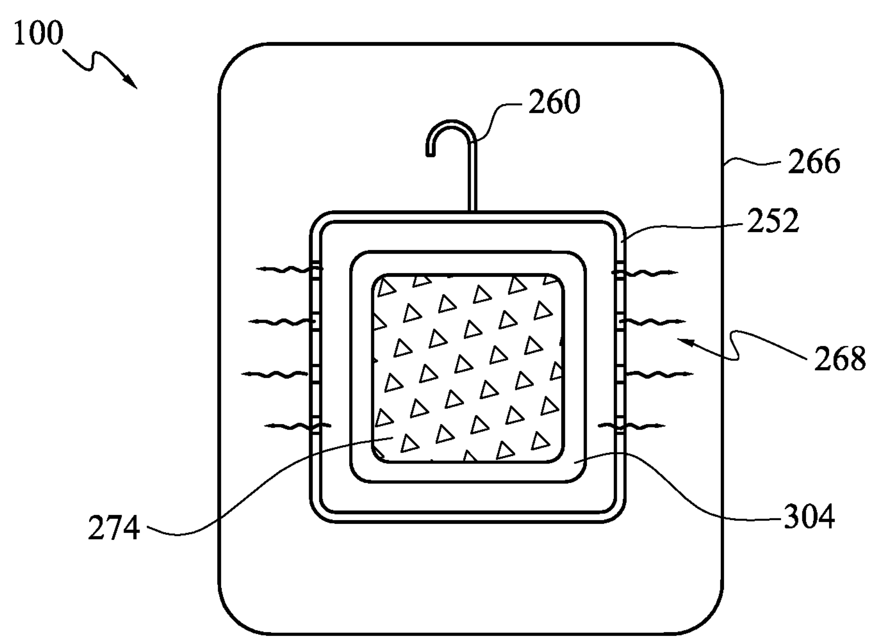

The emanator assembly 100 illustrated in FIG. 9 includes elements mentioned above, which are numbered accordingly. This emanator assembly 100 includes a thermally conductive porous treatment fluid-absorbing jacket 302. Jacket 302 is preloaded with a quantity of treatment fluid 120. After a user opens air-tight packaging 266, oxygen in the local atmosphere permeates into contact with exothermic material 274, and causes generation of heat. Treatment vapor 135 is consequently emitted through pores or apertures 268 for broadcast into the local environment.

Figure 10:
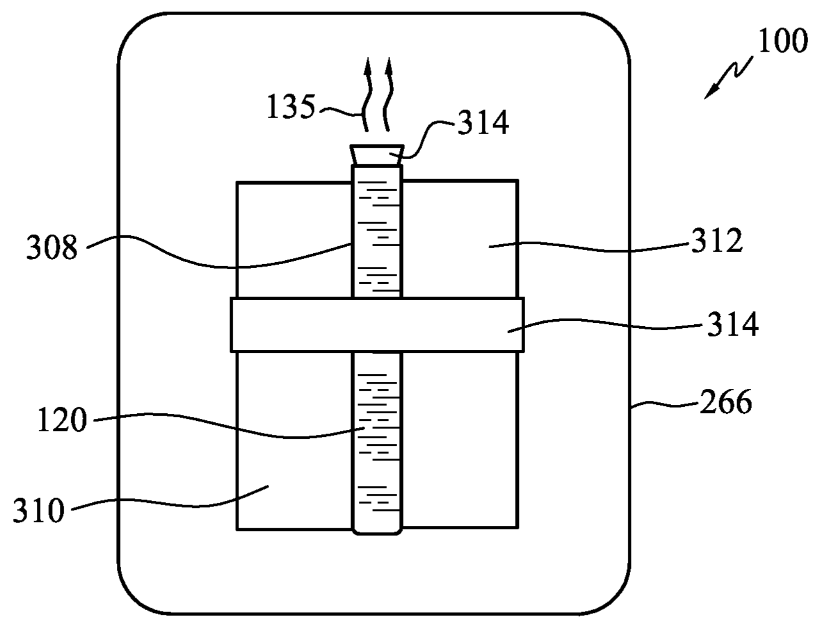

The emanator assembly 100 illustrated in FIG. 10 includes a fluid-holding container 308 disposed between first and second exothermic patches 310 and 312, respectively. In one embodiment, container 308 is a thermally conductive tube. An Aluminum tube works well. Treatment fluid 120 is retained inside the container 308 by a porous cap or plug 314. Treatment vapor 135 may pass through the plug 308 to treat the local environment. Patches 310, 312 may be held in operable association with container 308 by an assembly aide, such as a hook-and-loop strap. Activation of thermal patches 310, 312 by opening the air-tight packaging envelope 266 energizes the assembly 100, and emits treatment vapor at an enhanced rate.

Figure 11:
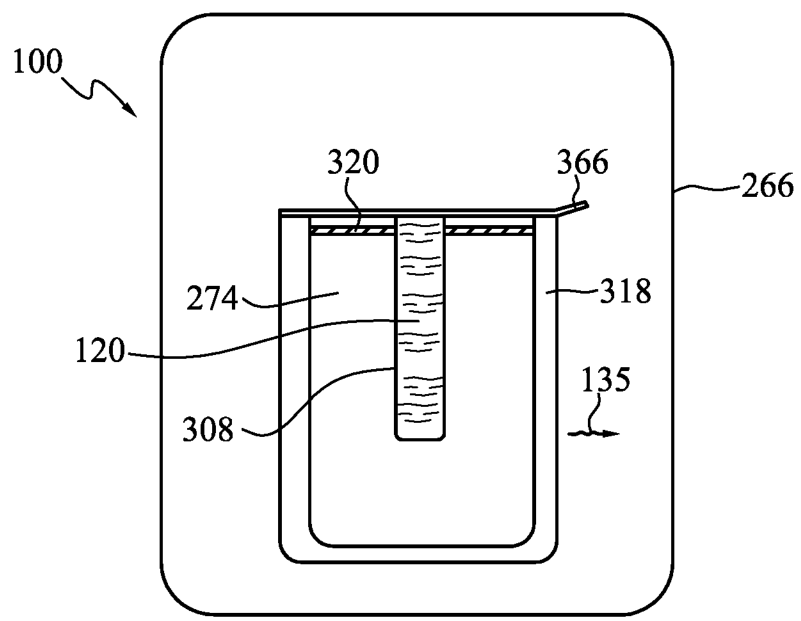

The emanator assembly 100 illustrated in FIG. 11 includes a thermally insulating porous cover or jacket 318 to hold a quantity of exothermic material 274. Cover 320 holds exothermic material 274 inside the jacket 318. Opening air-tight seal 266 starts an exothermic chemical reaction, and energizes the assembly 100. Treatment fluid 120 is heated by the exothermic reaction. Consequently, treatment vapor 135 is broadcast through jacket 318 to the local environment at an enhanced rate.

Figure 12:
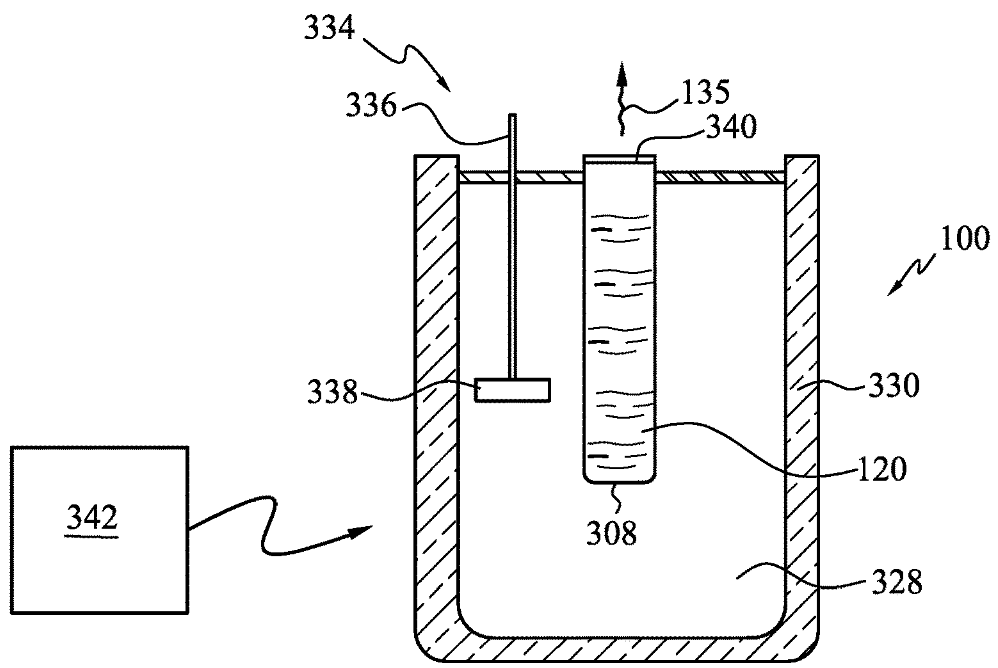

With reference to FIG. 12, another workable rechargeable energized emanator assembly 100 is disclosed. Saturated sodium acetate solution 328 confined inside a container 330 may be activated to produce an exothermic reaction by a user's operation of an activation mechanism, generally indicated at 334. For example, the activator slider 336 may be depressed to cause a metal scraper 338 to form nucleation or initiation sites for the saturated solution 328 to form crystals and release heat. The temperature may reach 55 degrees C., or so, and can be modulated with chemical attenuators. Heat applied to the treatment fluid 120 facilitates volatilization of fluid, and causes treatment vapor 135 to migrate through a porous plug 340 to the local atmosphere.

Still with reference to FIG. 12, a heat insulating container 330 may facilitate maintaining an elevated temperature in association with the treatment fluid 120 for an extended period of time. The solution 328 may be recharged by heating assembly 100 by a recharging source. A workable recharging source 342 includes boiling water, or microwaving the solution 328 to dissolve the crystals. Subsequently, the assembly 100 is ready for reuse.

Figure 13:
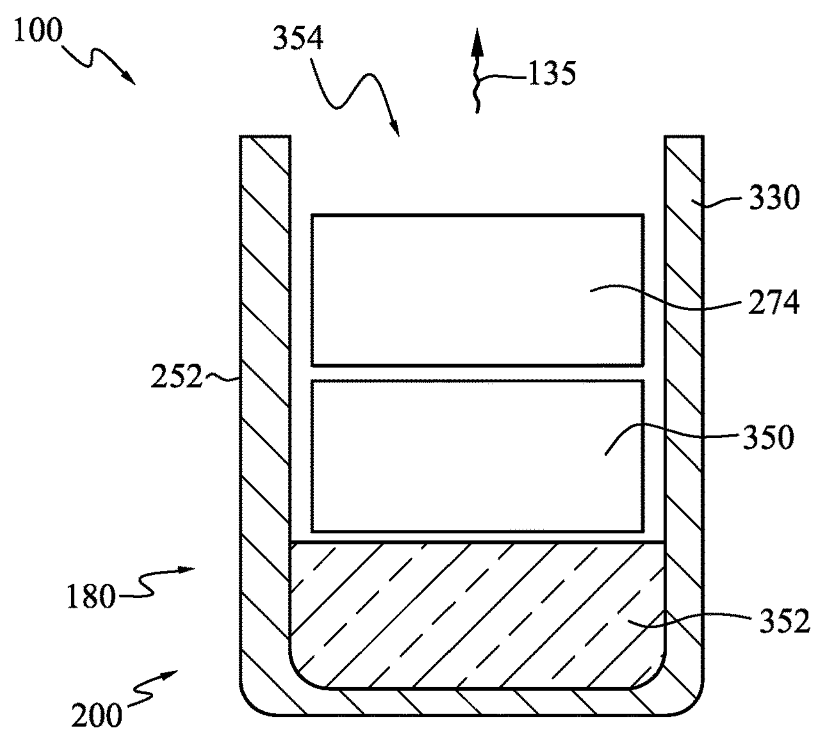

The energized emanator assembly 100 illustrated in FIG. 13 includes a thermally insulating container 330 arranged to hold a quantity of exothermic material 274' that includes exothermic material 274 premixed with a quantity of treatment fluid 120. Exothermic material 274' may, for examples, be in powder of block form. Suitable material of construction for a container 330 includes ceramic and plastic.

Still with reference to FIG. 13, assembly 100 includes an effervescent material 350 and a water source 352. A workable effervescent material may include citric acid and sodium bicarbonate. Water obtained from source 350 causes a gas-forming reaction, and enhances rate of discharge of vapor 135 from the discharge port, pore, aperture, or neck 354. A preferred water source resists presence of free water that can spill and make a mess. A workable water source includes an arrangement of water-jello or water beads, or sometimes a water-loaded powder or quantity of high surface area material. A water source may include CMC and water.

Figure 14:
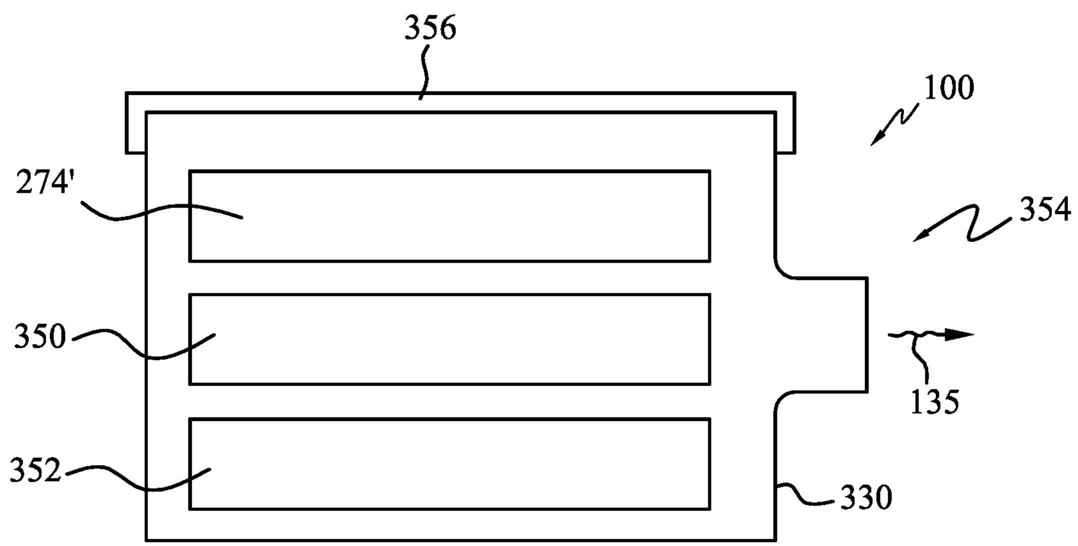

The energized emanator assembly 100 illustrated in FIG. 14 is structured similarly to that illustrated in FIG. 13. However, in FIG. 14 the container 330 is arranged as a box with an operable lid 356.

Figure 15:
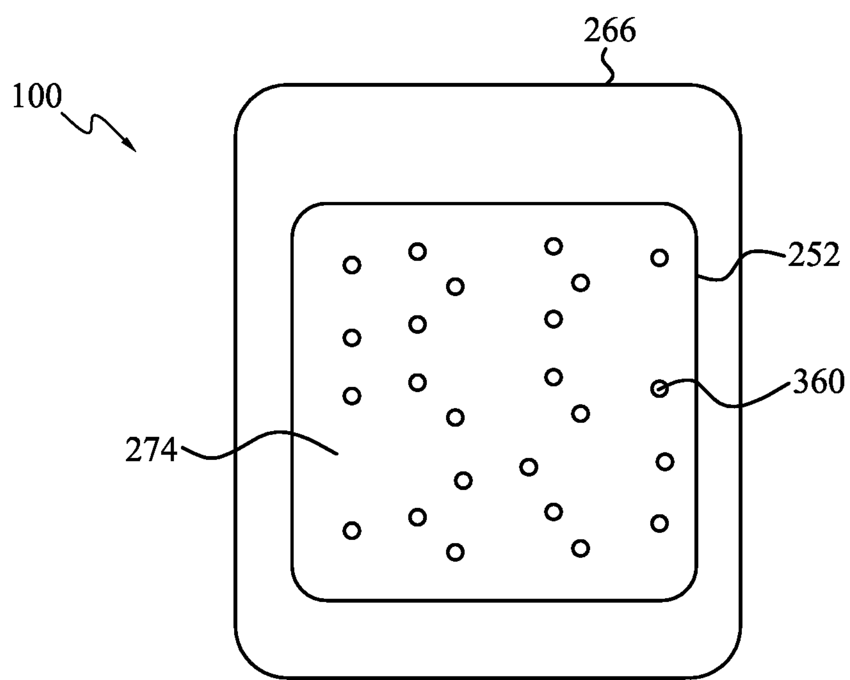

The embodiment 100 illustrated in FIG. 15 is exemplary of another energized emanator assembly according to certain principles of the invention. This assembly 100 includes an air-activated exothermic material 274 disposed inside a porous pouch-like container 252. Treatment fluid is combined with high surface area (HSA) material. As illustrated, the HSA material may be provided as a plurality of commercially available substantially round ceramic beads 360. However, HSA material in powder form and other geometric shapes is workable. An exothermic reaction is initiated when a user tears open the packaging material 266 at time of desired use of the assembly 100. Heat from the exothermic reaction facilitates volatization of treatment fluid dispersed inside the HSA material. Consequently, treatment fluid in vapor form 135 is applied to the local environment at an enhanced rate. An advantage of this assembly 100 is its inherent resistance to fluid spills and resulting mess.

Figure 16:
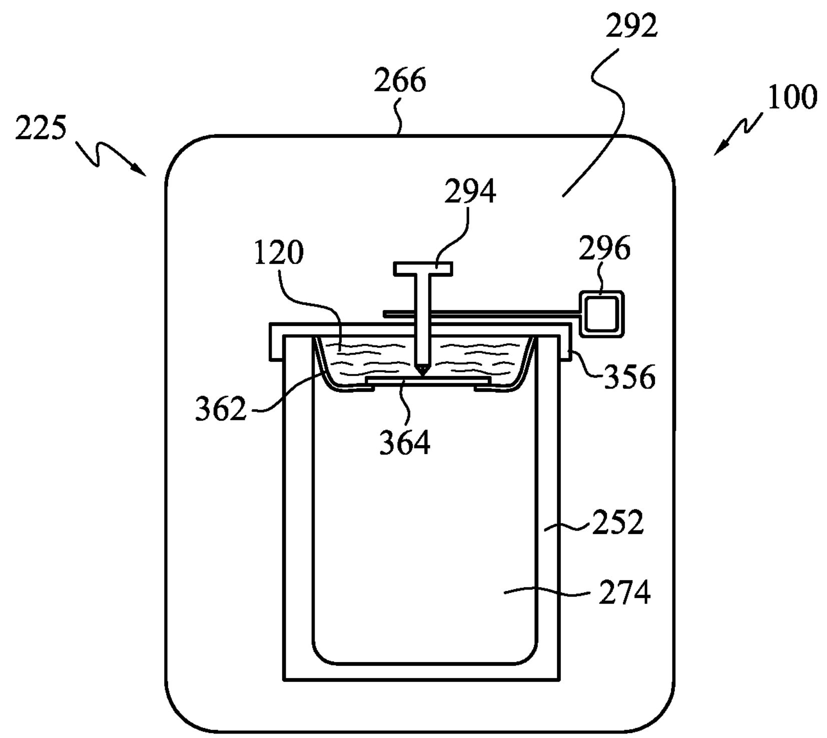

The embodiment 100 illustrated in FIG. 16 is exemplary of another energized emanator assembly according to certain principles of the invention. This emanator assembly 100 includes treatment fluid 120 that is stored in pocket 362 separately from the exothermic material 274. Pocket 362 is exemplary of a sequestering arrangement 225. After the air-tight package 266 is opened by a user, oxygen in the local atmosphere reacts with the exothermic material 274 and the exothermic reaction begins. The user then operates the actuator 294 to rupture the membrane 364, which may release fluid 120 for direct contact with either the exothermic material 274 or another workable emanator.

Figure 17:
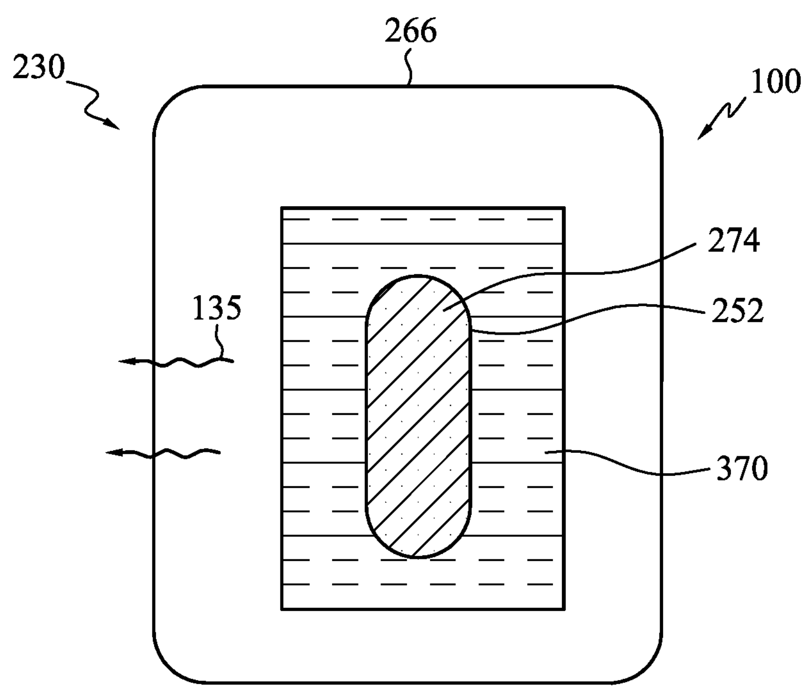

FIG. 17 illustrates an assembly 100 including a time-delay mechanism 230 that is constructed to cause energizing activity to begin, or to increase, after a period of time in use. In this case, the rate of emanation of a treatment fluid 10 can be enhanced at that time when its conventional (unenergized) emanation would be inherently reduced. In the illustrated arrangement, a boundary (sponge 370) is provided around a heat-producing material 274. As illustrated, exothermic material 274 is confined inside a porous pouch container 252, which is surrounded by sponge 370. A desired amount of treatment fluid 120 is dispersed or uptaken into sponge 370. The boundary defined by the sponge 370 resists activation of the heat-producing material 274 until a point in time where the emanation of vapor 135 from the sponge 370 is normally reduced, and subsequent addition of heat can then beneficially restore rate of emanation of vapor 135 of an emanating device to a higher (energized and enhanced) level.

One workable boundary element can include walls of cellulose sponge that are impregnated with treatment fluid. Another workable boundary includes encapsulating walls of high surface area material, such as ceramic, which are loaded with treatment fluid. Air may pass through a workable boundary material and into the exothermic mixture after a sufficient amount of treatment fluid 120 has evaporated, and a path for air ingress opens up.

In the embodiment 100 illustrated in FIG. 17, fluid molecules are depleted from the perimeter boundary of the sponge as the device ages (emanates), consequently permitting oxygen to penetrate into contact with and activate the heat-generating material. Produced heat increases emanation of the remaining treatment fluid, and tends to maintain emanation from the device closer to a constant level until the end of its useful life.

Figure 18:
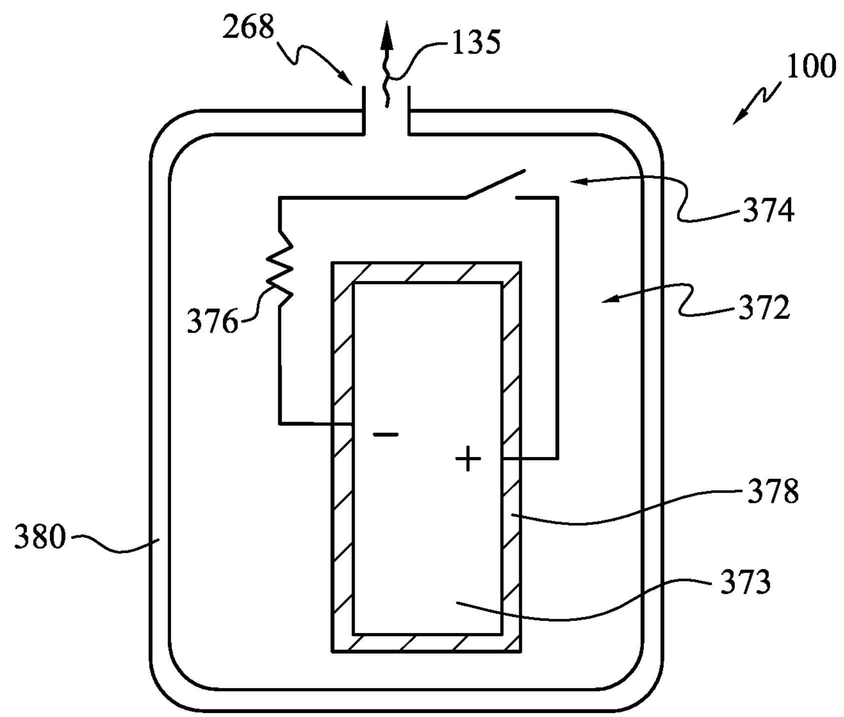

The embodiment of assembly 100 illustrated in FIG. 18 incorporates an energy storage device, generally 372, in-circuit to discharge stored energy and convert that energy to heat. The generated heat is harnessed to volatize a treatment fluid for broadcast of a treatment vapor 135 to a local environment. As illustrated, an energy storage device 372 such as a battery or capacitor may be placed in circuit through a switch 374 to a resistor element 376. The switch 374 may be closed at a point in time when vapor of treatment agent 135 is desired in the local environment. In the case of a battery 373, the electrical energy stored in the battery 373 is converted to heat. Heat may be generated by the resistor 376. When the resistor 376 has a sufficiently low resistance, the battery heats up due to high current draw (e.g., almost a short-circuit), and correspondingly heats up the surrounding carrier material 378 that holds a quantity of treatment substance 120. A workable thermal shield 380 may be constructed of polypropylene, or other material with thermal insulating qualities, to ensure generated heat is driven into the treatment fluid 120.

The carrier material 378 is desirably disposed for good thermal communication with the energy storing element or heat source 372. Broadly, a carrier material 378 may be considered as an absorber/emitter, because the carrier material 378 is loaded by treatment fluid 120 during manufacture of the assembly 100, then emits treatment in vapor form 135 during operation of the device 100. Workable materials of construction for a carrier material 378 include porous polymers, cotton fabric, felt, and the like.

Figure 19:
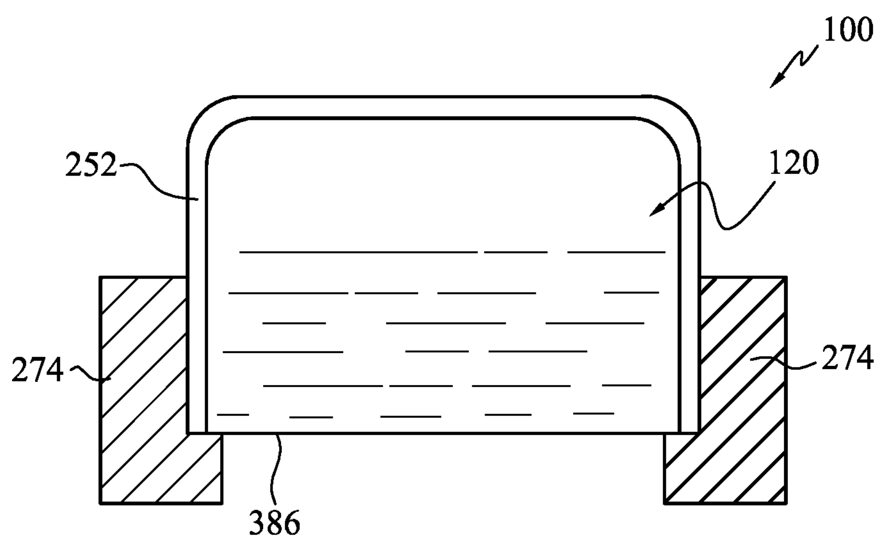

In the assembly 100 illustrated in FIG. 19, a fluid-holding container 252 holds a bulk quantity of volatile treatment substance 120 in fluid form and has a diffusion membrane 386 located to be wetted by the treatment substance 120 under the influence of gravity. A workable diffusion membrane 386 may be constructed from nano- or microporous polymer membrane material, including microporous polyethylene. One or more exothermic material 274 is distributed around a perimeter of the container 252 to provide heat to the container, and thereby enhance evolution of vapor 135 from the bulk fluid source of treatment vapor. This device 100 is sometimes configured for placement in an airstream, such as in association with an automobile's air vent or other source of air flow. The airstream also promotes broadcast of a fluid treatment substance in vapor form 135 into the local environment.

Figure 20:
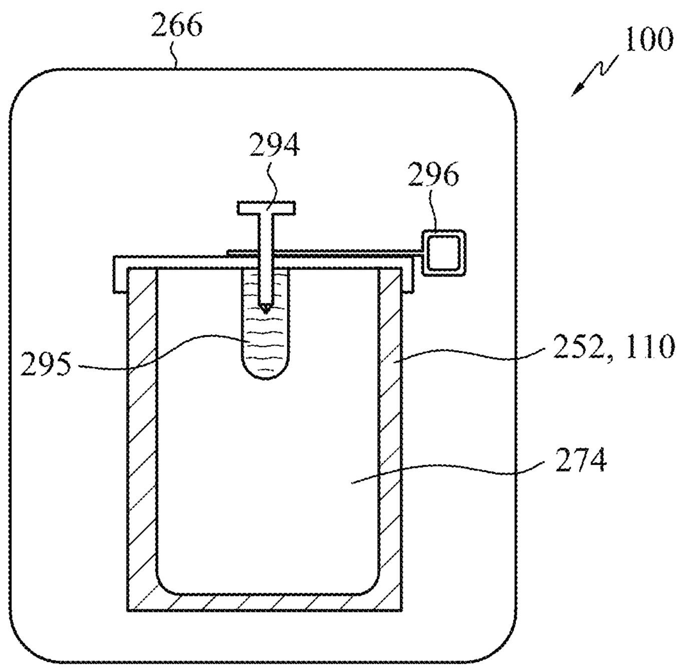

FIG. 20 illustrates an embodiment 100 constructed to start an exothermic reaction upon opening of the air-tight package 266. An exemplary thermal material mix 274 may be a dry exothermic mixture of Iron, NaCl, vermiculite and carbon similar to the mix contained in commercially available hand and body warmers. Moisture present in the local atmosphere is typically sufficient to initiate an exothermic reaction. The exothermic reaction may be accelerated by a user actuating the activating mechanism 294 to allow hydrogen peroxide or water to mix with the powdered dry exothermic mixture. It is recognized that Iron may be substituted by another metal, such as Aluminum, Magnesium, or Calcium. Further, NaCl may be substituted for by NaOCl. The temperature achieved by the exothermic mixture may be adjusted by the addition of water vs hydrogen peroxide, with the latter causing a hotter reaction. Treatment fluid 120 may be loaded into, or uptaken by, container 252, which can be an air permeable bag or other porous housing workable to confine the exothermic material 274.

Figure 21:
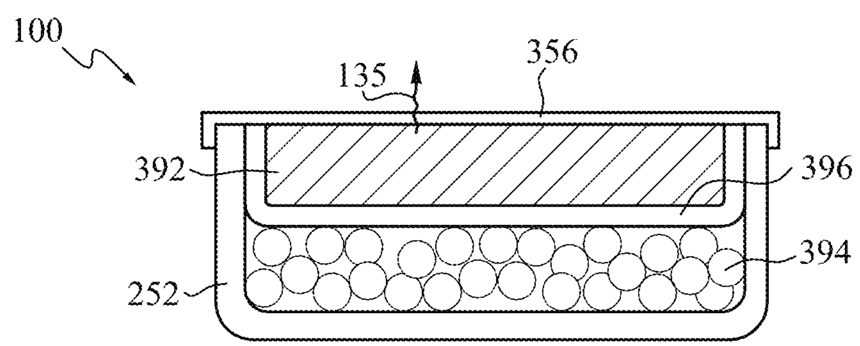

The energized assembly 100 illustrated in FIG. 21 includes a water-tight container 252 with internal partitions in which to hold an effervescent material 392 and water beads 394 in initial isolation from each other. Treatment fluid may be included in the mixture 392. Water beads 394 are commercially available under the name "water beads", and are compounds including a polymer. Water beads 394 are non-edible beads, made of a combination of water and a water-absorbing polymer. When dry water beads 394 are immersed in water, they fill up and expand like a sponge. When the effervescent material 392 contacts the water beads 394, a slow exothermic reaction begins. The reaction is slowed by the water beads' slow surrender of water to the reaction.

Still with reference to FIG. 21, lid 356 is sufficiently porous to permit off-gas release of treatment vapors. In one workable arrangement, container 252 and lid 356 are connected to confine the mix of treatment fluid 120 and effervescent material 392, and are sufficiently flexible to permit twisting of massaging the container 252 to rupture membrane 396. A ruptured membrane 396 permits the mixture 120/392 to contact water beads 394 and cause an exothermic reaction to energize dispersal of treatment vapor 135 into the local atmosphere.

Figure 22:
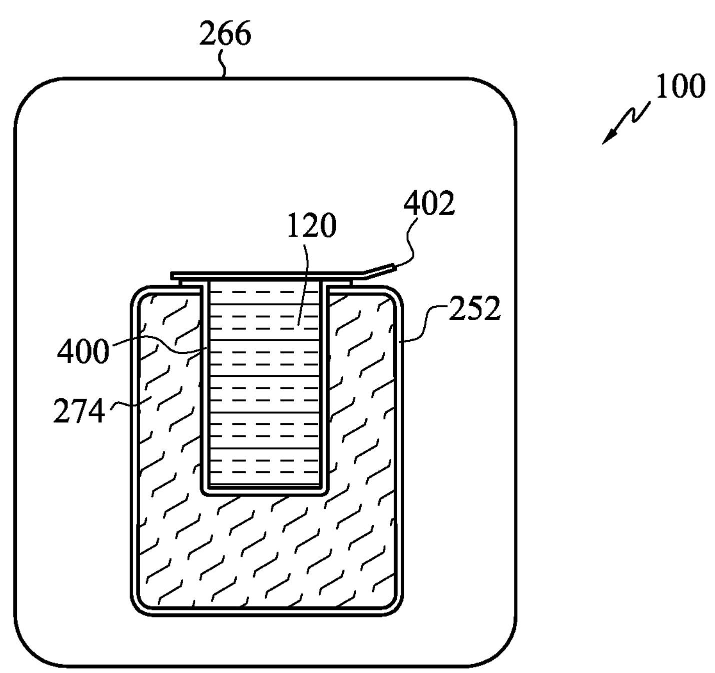

FIG. 22 illustrates an embodiment 100 which includes a thermally conductive cup or container 400 for improved heat transfer from an exemplary hand or body warmer-type exothermic device 130 into the fluid treatment substance 120. An exemplary container 400 may be made from metal having good thermal conductivity, such as Aluminum or copper. Treatment substance 120 may sometimes be in solidized form to resist fluid spills and mess. Opening the air-tight package 266 initiates the exothermic reaction, as described variously above. Treatment fluid in vapor form 135 may be emitted into the local atmosphere through a porous seal 402. Sometimes, an air-tight seal 402 may be removed, leaving behind a porous membrane or other element to resist spill of treatment fluid 120 while permitting escape of vapor 135.

Figure 23:
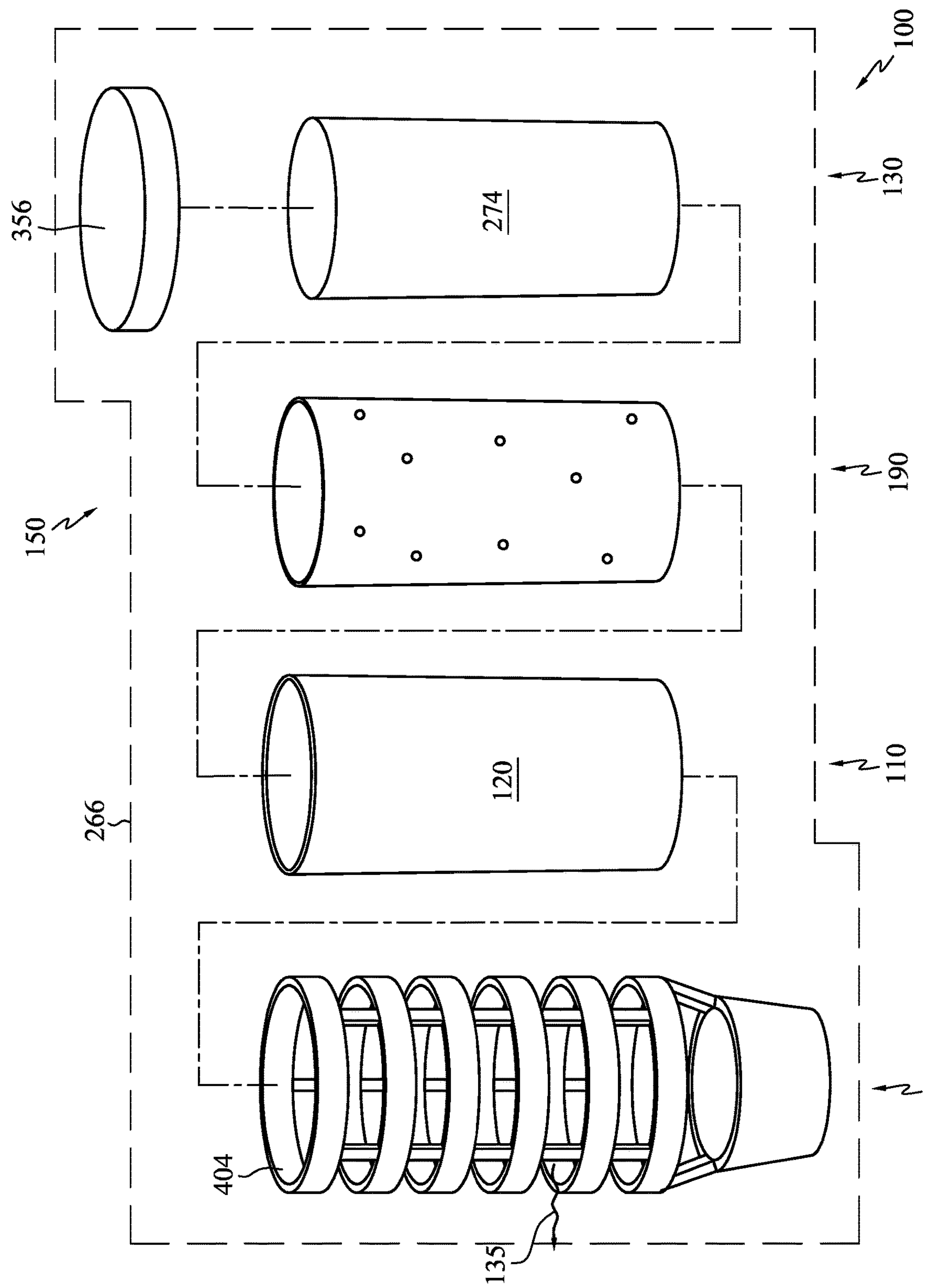
FIG. 23 is an exploded assembly view in perspective of a currently preferred embodiment within the ambit of FIG. 1.

The embodiment 100 illustrated in FIG. 23 is exemplary of another energized emanator assembly according to certain principles of the invention. This emanator assembly 100 includes a housing 140 configured to hold an emanator element 110. The housing 140 has a plurality of spaced-apart rails 404. Preferably, housing 140 is configured, in part, to provide a safety mechanism 170. In this illustration, safety mechanism 170 is to resist contact between a user and a potentially harmful ingredient of the assembly. For example, a gap between adjacent rails 404 can be too narrow or small to allow penetration of a child's tongue into the interior of the housing. A lid 356 or cap 406 may be configured to fit in permanent engagement over an access opening of the housing subsequent to manufacture assembly. The tamper-proof housing 140 in FIG. 23 is a configured upon assembly (of the cooperating cap 406 onto the housing 140), to resist nondestructive disassembly and unauthorized user access to e.g., the emanator element 110.

A workable housing 140 may be manufactured by injection molding from an inexpensive plastic material. Sometimes, a housing may be treated to provide, or its constituent material(s) may be inherently of, enhanced biodegradability. Certain housings 140 can form part of an assembly 100 that is regarded as disposable after a single use. For purpose of this disclosure, enhanced biodegradability means decompose in a landfill within 5 years.

With continued reference to FIG. 23, the illustrated and preferred emanator 110 is configured as a conical shell made of paper, or paper-like material, similar to a drinking cup. Emanator element 110 is exemplary of an element that is configured as a shell of revolution about an open core. Treatment fluid 120 may be dispersed into a volume of certain constituent material of the emanator 110. That treatment fluid 120 may then migrate toward and volatize at the surface of the emanator element 110 to broadcast vapor 135 to the local environment.

An optional heat conducting element 190 may be included in the assembly 100 of FIG. 23. A workable element 190 includes a metal foil, similar to tin foil. Sometimes, and as illustrated, the element 190 may be perforated. Other times, element 190 may be configured as an uninterrupted membrane, and can form a barrier for fluid migration from emanator 110 toward an energizing element 130.

Still with reference to FIG. 23, an energizing element 130 is configured for assembled reception inside the open core of emanator element 110. A currently preferred emanator element 130 includes a flameless mix of exothermic materials 274 such as described above. A removable gas barrier 150 is desirably included in association with the energizing element 130, in part, to resist undesired propagation of an exothermic reaction. For example, packaging envelope 266 can form a convenient air-tight arrangement to resist unintended actuation of the energizing element 130.

An embodiment according to certain aspects of the instant invention may be encompassed in a method to manufacture a device. One such method includes the step of providing an emanator having a surface area disposed in operable association with a volume. That method further includes the step of disposing a quantity of liquid treatment agent inside the volume to permit emanation of treatment fluid in vapor phase from the surface area. A further step includes disposing a quantity of an exothermic chemical mixture as a heat source in operable association with the volume to apply heat energy to the treatment agent therein to volatize the fluid and cause the enhanced emanation of treatment fluid in vapor phase from the surface. A preferred exothermic reaction is air-activated. Desirably, the quantity is configured and arranged to exothermically react for a period of time in excess of four hours subsequent to exposure to air. A further step may optionally include disposing a metallic thermally conductive element between the emanator and the heat source. A further step includes disposing the emanator, heat source, and conductive element inside of a housing comprising an aperture configured to dispense treatment vapor to a local environment. Sometimes, the housing may be configured to resist unauthorized contact with the emanator. A final step may include disposing the housing inside an air-tight envelope to delay production of heat until a user-selected instance in time.

While aspects of the invention have been described in particular with reference to certain illustrated embodiments, such is not intended to limit the scope of the invention. The present invention may be embodied in other specific forms without departing from its spirit or essential characteristics. For one example, one or more element may be extracted from one described or illustrated embodiment and used separately or in combination with one or more element extracted from one or more other described or illustrated embodiment(s), or in combination with other known structure. The described embodiments are to be considered as illustrative and not restrictive. Obvious changes within the capability of one of ordinary skill are encompassed within the present invention. All changes which come within the meaning and range of equivalency of the claims are to be embraced within their scope.

What is claimed is:

1. An apparatus, comprising:

an emanator with a surface area disposed in operable association with a volume;

a quantity of treatment agent disposed inside the volume to permit evaporation of treatment agent vapor from the surface area;

a flameless energizing heat source disposed in operable association with the volume to apply heat energy to the treatment agent therein; and a trigger mechanism configured to initiate an exothermic reaction associated with the heat source.

2. The apparatus according to claim 1, wherein:

the emanator comprises a material selected from the group consisting of cotton, paper, cellulose, woven textile or random mat or 3-dimensional structure comprising natural or synthetic fibers, natural or synthetic open or closed cell sponge, high surface area (HSA) materials having a surface area greater than 10 $m^2$/gm, diffusion membrane, and the like.

3. The apparatus according to claim 1, wherein:

the treatment agent is selected from the group consisting of scented oil, medicament, and insect repellant.

4. The apparatus according to claim 3, wherein:

the treatment agent is in a solidified form to resist spills and mess.

5. The apparatus according to claim 1, further comprising:

a housing configured to contain the emanator and the heat source, the housing comprising a plurality of apertures to permit migration of treatment agent in vapor phase from the surface area to a local environment.

6. The apparatus according to claim 5, wherein:
the housing is configured to define a safety perimeter to resist contact of the emanator with a child's mouth.

7. The apparatus according to claim 5, wherein:
the housing comprises a base configured to support the apparatus on top of a surface under the influence of gravity, an upstanding wall of the housing comprising the apertures.

8. The apparatus according to claim 5, wherein:
the housing further comprises a cap to cover a volume inside the upstanding wall; and
the housing and cap are configured to cooperate upon assembly of the apparatus to resist nondestructive disassembly and unauthorized access to the emanator.

9. The apparatus according to claim 5, wherein:
the housing comprises a hook configured to support the apparatus from a cooperating perch.

10. The apparatus according to claim 5, wherein:
the heat source is selected from the group consisting of chemicals arranged to generate an on-demand exothermic reaction, and an electrical circuit comprising a dry or wet cell battery or capacitor disposed in a heat-generating configuration.

11. The apparatus according to claim 1, further comprising:
a removable gas barrier arranged to resist initiation of an exothermic chemical reaction associated with the energizing heat source.

12. The apparatus according to claim 1, further comprising:
a time-delay mechanism to delay activation of the heat source until after a period of time subsequent to first deployment of the apparatus to treat a local environment.

13. The apparatus according to claim 1, further comprising:
a heat conducting element disposed between the heat source and the volume to facilitate heat transfer from the energizing heat source toward the volume.

14. The apparatus according to claim 13, wherein:
the heat conducting element is metallic foil.

15. The apparatus according to claim 1, further comprising:
a termination mechanism configured to resist further emanation of treatment agent in vapor state from the apparatus to permit reuse of the apparatus at a subsequent time.

16. The apparatus according to claim 1, further comprising:
a safety mechanism to resist user access to a harmful component of the apparatus.

17. The apparatus according to claim 16, wherein:
the safety mechanism comprises closely spaced apart louvers disposed around a perimeter of the housing.

18. An apparatus, comprising:
an emanator element configured as a shell of revolution about an open core, a volume of the shell to hold a treatment fluid, the open core to hold a flameless heat source;
a quantity of the treatment fluid disposed in the volume;
the heat source disposed in the open core, the heat source comprising an exothermic mixture of chemicals arranged for on-demand production of heat;
a heat conducting element disposed between the chemicals and the emanator element;
a housing with a plurality of spaced apart rails to provide a plurality of discharge apertures for a vapor of the treatment fluid, the housing being configured to resist disassembly and unauthorized access to the emanator element; and
an air-tight packaging envelope disposed to resist combination of oxygen from a local atmosphere with the exothermic chemicals.

19. An apparatus, comprising:
an emanator element comprising a volume to hold a treatment agent;
a quantity of the treatment agent disposed in solidized form within the volume;
a flameless heat source in operable association with the emanator, the heat source comprising an exothermic mixture of chemicals arranged for on-demand production of heat;
a heat conducting element disposed between the chemicals and the emanator element to promote application by the heat source of a uniform temperature profile onto the emanator;
a housing configured to hold the emanator element in operable association with the heat source, the housing comprising a plurality of discharge apertures for a vapor of the treatment agent, the housing being configured to resist disassembly and unauthorized access to the emanator element;
a trigger mechanism to cause the heat source to generate heat on-demand;
a safety mechanism to resist undesired operation of the trigger mechanism;
a gas generating element to enhance flow of treatment agent in vapor phase from the apertures;
a termination mechanism to interrupt generation of heat by the heat source to permit reuse of the apparatus at a subsequent time;
a sequestering arrangement to hold a first ingredient out of contact with a second ingredient prior to actuation of the trigger mechanism; and
an air-tight packaging envelope disposed to resist combination of an activation ingredient with the exothermic chemicals.

20. A method, comprising:
providing an emanator with a surface area disposed in operable association with a volume;
disposing a quantity of treatment agent inside the volume to permit emanation of treatment agent in vapor phase from the surface area;
disposing a quantity of an air-activated or water-activated exothermic chemical mixture as a heat source in operable association with the volume to apply heat energy to the treatment agent therein to volatize the agent and cause the enhanced emanation of treatment agent in vapor phase from the surface, the quantity being configured and arranged to exothermically react for a period of time in excess of four hours subsequent to exposure to air or water;
disposing a metallic thermally conductive element between the emanator and the heat source;
disposing the emanator, heat source, and conductive element inside of a housing comprising an aperture configured to dispense treatment vapor to a local environment, the housing to resist unauthorized contact with the emanator; and
disposing the housing inside an air-tight envelope.

* * * * *